(12) United States Patent
Katchen et al.

(10) Patent No.: US 8,608,038 B2
(45) Date of Patent: Dec. 17, 2013

(54) ADJUSTABLE ACCESSORY FOR ATTACHMENT TO A MOBILE DEVICE THAT ENHANCES MOBILITY OF AN INDIVIDUAL AND METHOD OF ASSEMBLING SAME

(76) Inventors: Michael Katchen, Fort Mill, SC (US); Theresa Katchen, Fort Mill, SC (US)

( * ) Notice: Subject to any disclaimer, the term of this patent is extended or adjusted under 35 U.S.C. 154(b) by 1215 days.

(21) Appl. No.: 12/218,731

(22) Filed: Jul. 17, 2008

(65) Prior Publication Data

US 2009/0020575 A1    Jan. 22, 2009

Related U.S. Application Data

(60) Provisional application No. 60/961,045, filed on Jul. 18, 2007.

(51) Int. Cl.
*B60R 7/00* (2006.01)
(52) U.S. Cl.
USPC ....... 224/407; 224/275; 224/552; 297/188.01
(58) Field of Classification Search
USPC ............ 224/407, 275, 552, 563; 297/188.01, 297/188.21; 296/37.16; 280/727; 248/316.1, 682, 689, 690
See application file for complete search history.

(56) References Cited

U.S. PATENT DOCUMENTS

| | | | | |
|---|---|---|---|---|
| 2,708,062 A | * | 5/1955 | Poyer | 224/275 |
| 2,783,896 A | * | 3/1957 | Agostini et al. | 211/64 |
| 3,765,635 A | * | 10/1973 | Burrell et al. | 248/313 |
| 3,970,344 A | | 7/1976 | Baumann | |
| 4,213,648 A | | 7/1980 | Steichen | |
| 4,438,764 A | | 3/1984 | Eppolito | |
| 4,506,903 A | | 3/1985 | Bowermaster | |
| 4,696,420 A | | 9/1987 | Kulik | |
| 4,848,714 A | * | 7/1989 | Ziaylek et al. | 248/313 |
| 4,865,237 A | * | 9/1989 | Allen | 224/552 |
| 5,012,963 A | | 5/1991 | Rosenbaum | |
| D319,778 S | * | 9/1991 | Ziaylek, Jr. | D8/373 |
| D342,222 S | | 12/1993 | Cherry | |
| 5,288,001 A | | 2/1994 | Locarno | |
| 5,340,140 A | | 8/1994 | Bynum | |
| 5,476,432 A | | 12/1995 | Dickens | |
| 6,220,557 B1 | * | 4/2001 | Ziaylek et al. | 248/316.1 |

(Continued)

FOREIGN PATENT DOCUMENTS

FR    2867663    9/2005

OTHER PUBLICATIONS

"Oxygen Bottle Holder" accessory for wheelchair; Web site http://www.electricscooter.com.au/products_electric_scooters.asp?category_id=5; Mobility Aids, Melbourne, Australia.

*Primary Examiner* — Gary Elkins
(74) *Attorney, Agent, or Firm* — Walter S. Stevens

(57) ABSTRACT

An adjustable accessory for attachment to a mobile device that enhances mobility of an individual and method of assembling same. In one embodiment, the adjustable accessory comprises a frame including a movable platform for adjusting height of a container thereon, such as an oxygen bottle. The adjustable accessory further comprises an adjustable strap connected to the frame and relocatable thereon, which strap at least partially encircles the container for adjustably securing containers of various diameters to the frame. The frame is adapted to be connected to the mobile device, which may be a wheelchair, walker, vehicle seat or other supporting structure. In this manner, an individual requiring a supply of oxygen due to a breathing ailment can suitable use the supply of oxygen while traveling in the mobile device.

21 Claims, 17 Drawing Sheets

(56) References Cited

U.S. PATENT DOCUMENTS

| | | |
|---|---|---|
| 6,672,321 B2 | 1/2004 | Hamilton |
| 6,926,243 B1 * | 8/2005 | Ziaylek et al. ............... 248/307 |
| 7,188,855 B1 * | 3/2007 | Thomas ..................... 280/304.1 |
| 7,637,404 B1 * | 12/2009 | Stepanova .................... 224/275 |
| 2006/0016466 A1 | 1/2006 | Carroll |
| 2006/0076820 A1 * | 4/2006 | Lackore .................. 297/452.29 |
| 2008/0190947 A1 * | 8/2008 | Bourgraf ...................... 220/737 |

\* cited by examiner

ADJUSTABLE ACCESSORY FOR ATTACHMENT TO A MOBILE DEVICE THAT ENHANCES MOBILITY OF AN INDIVIDUAL AND METHOD OF ASSEMBLING SAME

CROSS REFERENCE TO RELATED APPLICATIONS

Reference is hereby made to the following U.S. Provisional patent application whereof the benefit is hereby claimed and the disclosure hereby incorporated in its entirety by reference: U.S. Provisional patent application No. 60/961,045, titled "AIR JOCKEY" and filed Jul. 18, 2007 in the names of Michael Katchen and Theresa Katchen.

BACKGROUND

This application generally relates to supports, such as stands and brackets, and more particularly relates to an adjustable accessory for attachment to a mobile device that enhances mobility of an individual and method of assembling same.

Individuals with breathing or respiratory disorders, which may be due to medical ailments such as chronic obstructive pulmonary disease, acute bronchitis, allergies, asthma, emphysema or other breathing disorders, often require a breathing aide, such as an oxygen dispensing device (e.g., oxygen bottle). Breathing oxygen from the oxygen dispensing device allows individuals with the breathing disorder to inhale a sufficient supply of oxygen to mitigate symptoms of the breathing disorder. Such individuals often require a continuous supply of oxygen when performing their daily routines, such as shopping, outdoor excursions, traveling in vehicles, and the like. Moreover, due to reduced physical stamina, such individuals often must use a wheelchair or walker when performing their daily routines.

Attempts have been made to provide individuals with a source of oxygen while using wheelchairs and walkers. For example, U.S. Pat. No. 3,970,344, issued in the name of Arthur V. Baumann and titled "Oxygen Tank Holder For Wheelchairs" discloses an oxygen tank holding device for ready attachment to most standard, foldable wheelchairs. According to this patent, the device frees respiratory patients from confinement by providing them with available oxygen mounted on their wheelchairs. Although this patent discloses an oxygen tank holding device for ready attachment to most standard, foldable wheelchairs, this patent does not appear to disclose an adjustable accessory for attachment to a device that enhances mobility of an individual and method of assembling same, as described and claimed herein.

Another example is disclosed in U.S. Pat. No. 4,506,903 issued in the name of Sidney P. Bowermaster and titled "Wheelchair Attachment." This patent discloses a device for detachably coupling a wheeled oxygen tank cart to a wheelchair such that they are transportable together as a unit without need of a separate operator of the cart. The device is adjustable in length such that various sizes of wheelchairs may be accommodated. Although this patent discloses a device for detachably coupling a wheeled oxygen tank cart to a wheelchair such that they are transportable together as a unit without need of a separate operator of the cart and also discloses that the device is adjustable in length such that various sizes of wheelchairs may be accommodated, this patent does not appear to disclose an adjustable accessory for attachment to a device that enhances mobility of an individual and method of assembling same, as described and claimed herein.

Yet another example is disclosed in U.S. Pat. No. 4,696,420 issued in the name of Helmut Kulik and titled "Oxygen Carrier." This patent discloses a device for detachable coupling an oxygen carrier to a wheelchair such that they are transportable together as a unit without need of a separate operator of the cart. The carrier is made in different lengths depending on the size of the wheelchair. Although this patent discloses a device for detachable coupling an oxygen carrier to a wheelchair such that they are transportable together as a unit without need of a separate operator of the cart and that the carrier is made in different lengths depending on the size of the wheelchair, this patent does not appear to disclose an adjustable accessory for attachment to a device that enhances mobility of an individual and method of assembling same, as described and claimed herein.

None of the art recited hereinabove appears to disclose an adjustable accessory for attachment to a device that enhances mobility of an individual and method of assembling same, as described and claimed herein.

Therefore, what is needed is an adjustable accessory for attachment to a device that enhances mobility of an individual and method of assembling same.

SUMMARY

According to an aspect of this disclosure, there is provided an adjustable accessory for attachment to a device that enhances mobility of an individual, comprising a frame capable of being coupled to the device; and an adjustment mechanism coupled to the frame, the adjustment mechanism capable of being sized to adjustably surround a container to be carried by the frame and capable of adjustably locating the container on the frame.

According to another aspect of this disclosure, there is provided an adjustable accessory for attachment to a device that enhances mobility of an individual, comprising a frame having a plurality of holes for receiving respective ones of a plurality of fasteners; and a strap engageable with the frame and the container for coupling the container to the frame, the strap having an aperture for receiving a predetermined one of the fasteners as the predetermined one of the fasteners is received in a respective one of the plurality of holes, whereby the strap is adjustably affixed to the frame as the predetermined one of the fasteners is received by the aperture.

According to another aspect of the disclosure there is provided an adjustable accessory for attachment to a device that enhances mobility of an individual while the adjustable accessory securely carries a container, comprising a frame having a plurality of holes for receiving respective ones of a plurality of fasteners therethrough; and a strap engageable with the frame and capable of at least partially encircling the container for coupling the container to the frame, the strap having an aperture for receiving a predetermined one of the fasteners therethrough as the predetermined one of the fasteners is received through a respective one of the holes, whereby the strap is adjustably affixed to the frame as the predetermined one of the fasteners is received through the aperture.

According to yet another aspect of the disclosure, there is provided an adjustable accessory for attachment to a device that enhances mobility of an individual while the adjustable accessory securely carries a container having a substance therein of medicinal benefit to the individual, comprising a frame having a plurality of holes for receiving respective ones of a plurality of fasteners; a strap engageable with the frame and sized to at least partially encircle the container for connecting the container to the frame, the strap having an aperture therethrough alignable with a predetermined one of the fasteners for receiving the predetermined one of the fasteners therethrough as the predetermined one of the fasteners is received through a respective one of the holes, whereby the strap is adjustably affixed to the frame as the predetermined one of the fasteners is received through the aperture and whereby the container is adjustably securely carried by the frame as the predetermined one of the fasteners is received through the respective one of the holes and as the strap is adjustably affixed to the frame; and an adjustable platform integrally connected to the frame for adjustably supporting the container on the platform.

According to an additional aspect of the disclosure, there is provided a device enhancing mobility of an individual, comprising an adjustable accessory, including a frame capable of being coupled to the device; and an adjustment mechanism coupled to the frame, the adjustment mechanism capable of being sized to adjustably surround a container to be carried by the frame and capable of adjustably locating the container on the frame.

According to a further aspect of the disclosure, there is provided a device that enhances mobility of an individual, comprising an adjustable accessory, including a frame having a plurality of holes for receiving respective ones of a plurality of fasteners; and a strap engageable with the frame and the container for coupling the container to the frame, the strap having an aperture for receiving a predetermined one of the fasteners as the predetermined one of the fasteners is received in a respective one of the holes, whereby the strap is adjustably affixed to the frame as the predetermined one of the fasteners is received by the aperture.

According to yet another aspect of the disclosure, there is provided a device that enhances mobility of an individual while the accessory securely carries a container having a substance therein of medicinal benefit to the individual, comprising an adjustable accessory, including a frame having a plurality of holes for receiving respective ones of a plurality of fasteners therethrough; a strap engageable with the frame and sized to at least partially encircle the container for connecting the container to the frame, the strap having an aperture therethrough alignable with a predetermined one of the fasteners for receiving the predetermined one of the fasteners therethrough as the predetermined one of the fasteners is received through a respective one of the holes, whereby the strap is adjustably affixed to the frame as the predetermined one of the fasteners is received through the aperture and whereby the container is adjustably securely carried by the frame as the predetermined one of the fasteners is received through the respective one of the holes and as the strap is adjustably affixed to the frame; and an adjustable platform integrally connected to the frame for adjustably supporting the container on the platform.

According to another aspect of the disclosure, there is provided a method of assembling an adjustable accessory for attachment to a device that enhances mobility of an individual, comprising providing a frame capable of being coupled to the device; and coupling an adjustment mechanism to the frame, the adjustment mechanism capable of being sized to adjustably surround a container to be carried by the frame and capable of adjustably locating the container on the frame.

According to another aspect of the disclosure, there is provided a method of assembling an adjustable accessory for attachment to a device that enhances mobility of an individual, comprising providing a frame having a plurality of holes for receiving respective ones of a plurality of fasteners; and engaging a strap with the frame and the container for coupling the container to the frame, the strap having an aperture for receiving a predetermined one of the fasteners as the predetermined one of the fasteners is received in a respective one of the holes, whereby the strap is adjustably affixed to the frame as the predetermined one of the fasteners is received by the aperture.

According to an additional aspect of the disclosure, there is provided a method of assembling an adjustable accessory for attachment to a device that enhances mobility of an individual while the adjustable accessory securely carries a container, comprising providing a frame having a plurality of holes for receiving respective ones of a plurality of fasteners therethrough; and engaging a strap with the frame, the strap capable of at least partially encircling the container for coupling the container to the frame, the strap having an aperture for receiving a predetermined one of the fasteners therethrough as the predetermined one of the fasteners is received through a respective one of the holes, whereby the strap is adjustably affixed to the frame as the predetermined one of the fasteners is received through the aperture.

According to another aspect of the disclosure, there is provided a method of assembling an adjustable accessory for attachment to a device that enhances mobility of an individual while the accessory securely carries a container having a substance therein of medicinal benefit to the individual, comprising providing a frame having a plurality of holes for receiving respective ones of a plurality of fasteners therethrough; engaging a strap with the frame, the strap sized to at least partially encircle the container for connecting the container to the frame, the strap having an aperture therethrough alignable with a predetermined one of the plurality of the fasteners for receiving the predetermined one of the fasteners therethrough as the predetermined one of the fasteners is received through a respective one of the holes, whereby the strap is adjustably affixed to the frame as the predetermined one of the fasteners is received through the aperture and whereby the container is adjustably securely carried by the frame as the predetermined one of the fasteners is received through the respective one of the holes and as the strap is adjustably affixed to the frame; and integrally connecting an adjustable platform to the frame for adjustably supporting the container on the platform.

A feature of the present disclosure is the provision of a frame having a plurality of holes for receiving respective ones of a plurality of fasteners for attaching the frame to a mobile device.

Another feature of the present disclosure is the provision of an adjustable strap engageable with the frame and a container for coupling the container to the frame.

A further feature of the present disclosure is the provision of an adjustable platform belonging to the frame for adjustably supporting the container at various elevations on the frame.

In addition to the foregoing, various other method and/or device aspects are set forth and described in the teachings, such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

While the specification concludes with claims particularly pointing-out and distinctly claiming the subject matter of the present disclosure, it is believed the disclosure will be better understood from the following detailed description when taken in conjunction with the accompanying drawings. In addition, the use of the same symbols in different drawings will typically indicate similar or identical items.

DETAILED DESCRIPTION

Figure 1:
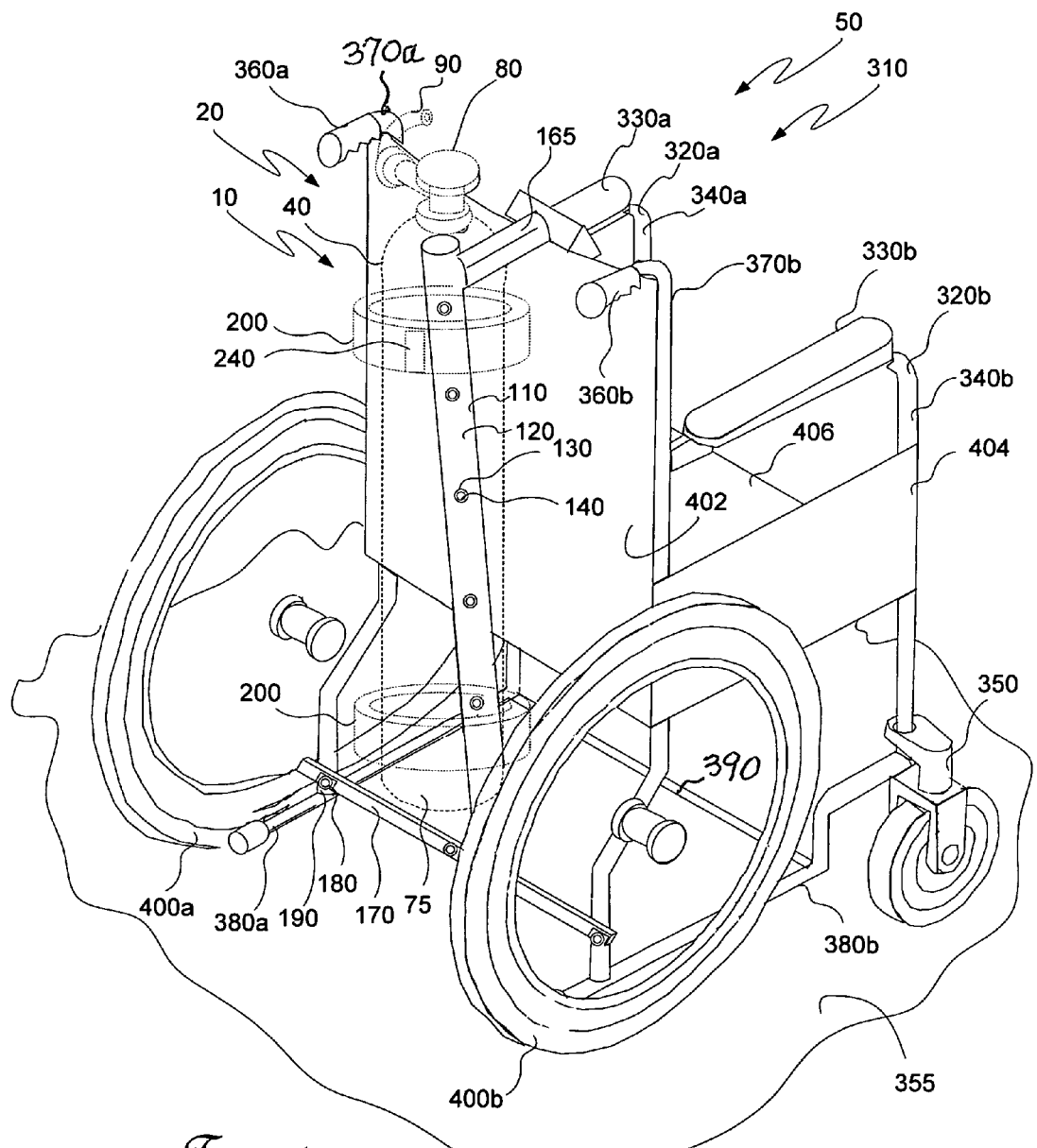
FIG. 1 is a view in perspective of a first embodiment adjustable accessory adjustably connected to a first embodiment mobile device, with parts removed for clarity.
Figure 2:
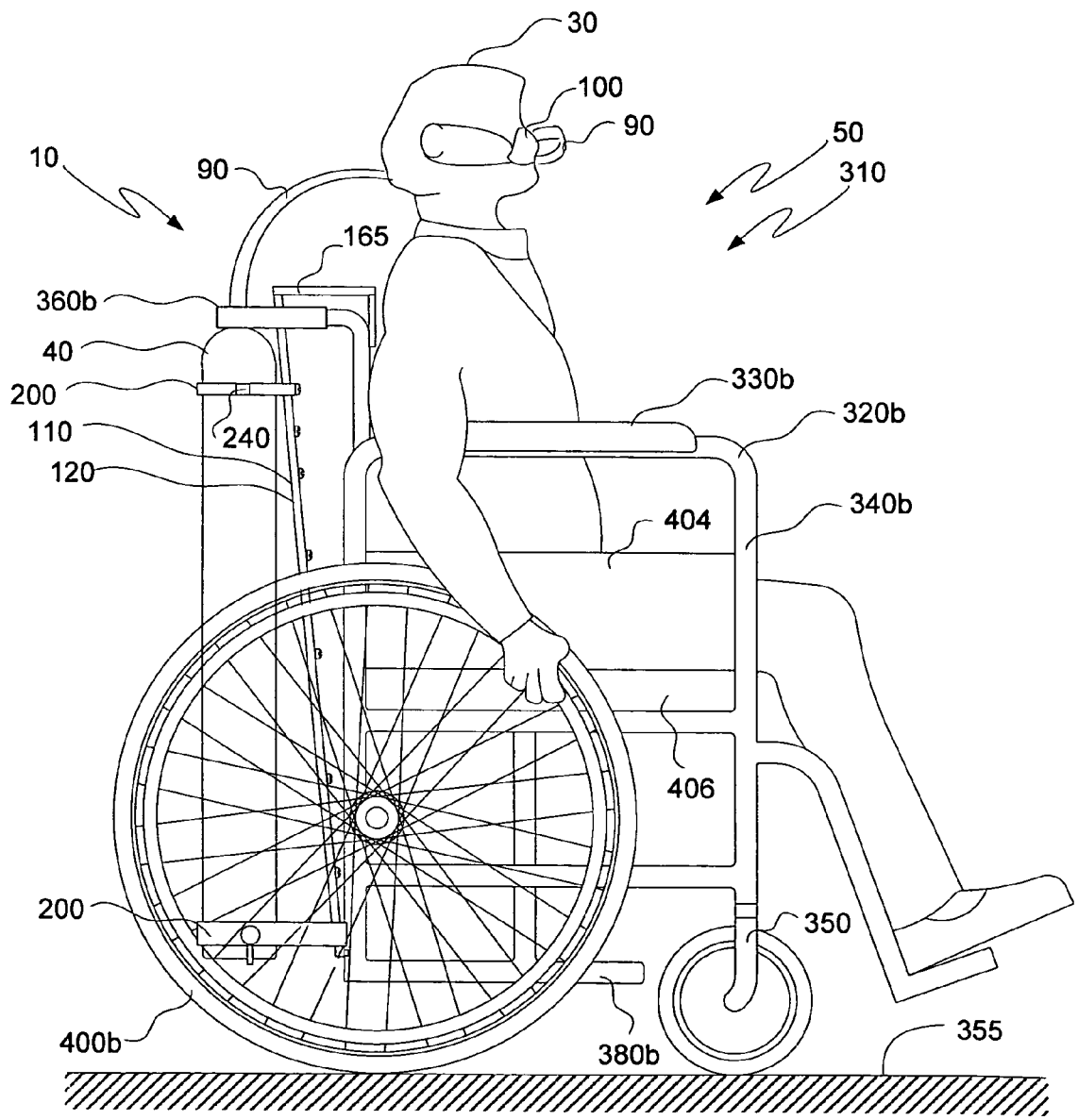
FIG. 2 is a view in elevation of the first embodiment adjustable accessory connected to the first embodiment mobile device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein.

In addition, the present application uses formal outline headings for clarity of presentation. However, it is to be understood that the outline headings are for presentation purposes, and that different types of subject matter may be discussed throughout the application (e.g., device(s)/structure(s) may be described under process(es)/operations heading(s) and/or process(es)/operations may be discussed under structure(s)/process(es) headings; and/or descriptions of single topics may span two or more topic headings). Hence, the use of the formal outline headings is not intended to be in any way limiting.

Moreover, the herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

Applicants have observed that a problem in the art is reduced mobility for an individual while manually carrying an oxygen dispensing device or oxygen bottle. For example, a typical "B" or "M-6" size aluminum compressed oxygen bottle is approximately 3.21 inches in diameter, 5.37 inches in height, has a capacity of 164 liters and weighs 2.2 pounds (empty weight without valve or oxygen). A valve for the oxygen bottle, such as a CGA 870 type valve, can weigh an additional 11 ounces. A larger size of aluminum compressed oxygen bottle is the "E" or "M-24", which is approximately 4.38 inches in diameter, 24.9 inches in height, has a capacity of 680 liters and weighs 7.9 pounds (empty weight without valve or oxygen). Hence, manually carrying and handling of the oxygen bottle by a person of reduced stamina, such as a person having a breathing ailment, requires significant energy and consequently interferes with that person's mobility. Therefore, it is desirable to provide means for more easily carrying the oxygen bottle without need to manually carry the oxygen bottle on one's person while performing one's daily routine.

Even when the oxygen bottle is attached to a wheelchair, walker, vehicle seat or other mobile devices and supporting structures, another problem in the art is absence of an adjustable mechanism for conveniently carrying the oxygen bottle on the wheelchair, walker or vehicle seat. In this regard, oxygen bottles, wheelchairs, walkers and vehicle seats are manufactured in various sizes and configurations. A versatile mechanism for carrying the oxygen bottle would be able to accommodate these various sizes and configurations. Therefore, it is desirable to provide a versatile mechanism for conveniently carrying the oxygen bottle in a manner that would accommodate various sizes and configurations of oxygen bottles, wheelchairs, walkers, vehicle seats and other mobile devices and supporting structures.

The present disclosure addresses the problems recited hereinabove. In addition, it will be understood that although particular embodiments are disclosed herein, other embodiments are possible as well, based on the teachings of this disclosure. Thus, the present disclosure is intended to embrace all such other embodiments.

Therefore, referring to FIGS. 1, 2, 3, 4, 4A, 5 and 6, there is shown a first embodiment adjustable accessory, generally referred to as 10, for attachment to a mobile device or supporting structure, generally referred to as 20. Device 20 enhances mobility of an individual 30 who occupies device 20, while the adjustable accessory 10 securely carries a container 40 having a substance (not shown) therein of medicinal benefit to individual 30. As described in more detail hereinbelow, device 20 may be, without limitation, a wheelchair, generally referred to as 50, a walker, generally referred to as 60, or a vehicle seat, generally referred to as 70.

Referring again to FIGS. 1, 2, 3, 4, 4A, 5 and 6, container 40, which has a base portion 75, may be a generally cylindrical oxygen tank or bottle, such as a "B" or "M-6" size aluminum compressed oxygen bottle, an "E" or "M-24" size aluminum compressed oxygen bottle or other size compressed oxygen bottle chosen by individual 30. As described in detail hereinbelow, adjustable accessory 10 is configured to adjustably accommodate various sizes of oxygen bottles. Container 40 comprises a metering valve 80 for metering oxygen to individual 30. Container 40 further comprises a tube 90 for supplying the metered oxygen to a respirator 100 worn by individual 30. Although container 40 is described herein as containing oxygen, it should be appreciated that container 40 may contain another substance of medicinal benefit to individual 30. In this regard, container 40 may contain a fluid to be supplied to individual 30 intravenously. In this case, adjustable accessory 10 would allow elevation of container 40 to an appropriate height relative to the position of individual 30, so that the fluid is supplied to individual 30 by force of gravity. Moreover, container 40 may be a monitor containing electronic circuitry (not shown) and a power supply (also not shown) for monitoring vital functions of individual 30, such as monitoring breathing rate or heart rate of individual 30.

Still referring to FIGS. 1, 2, 3, 4, 4A, 5 and 6, first embodiment adjustable accessory comprises a frame 110 including an elongate spine 120 that has a plurality of holes 130 therethrough. It should be appreciated that frame 110 includes holes 130 because frame 110 includes spine 120. Holes 130 receive respective ones of a plurality of fasteners 140. Each fastener 140 may comprise, without limitation, a threaded bolt member 150 sized to receive a threaded nut 160 on an end portion thereof. Threaded bolt member 150 is affixed to spine 120 as threaded nut 160 threadably engages the end portion of threaded bolt member 150. Integrally connected to an end portion of spine 120 is a J-shaped or L-shaped hook remember 165 for coupling frame 110 to a mobile device, such as a back of a wheelchair, a cross-bar of a walker, or vehicle seat. In addition, J-shaped or L-shaped hook member 165 is capable of coupling frame 110 to any other suitable supporting structure, such a chair, park bench or the like. Moreover, although spine 120 is shown as having a circular transverse cross-section, spine 120 may have any suitable transverse cross-section, such as a rectangular or square transverse cross-section.

Referring yet again to FIGS. 1, 2, 3, 4, 4A, 5 and 6, frame 110 also includes a cross-member or bracket 170 integrally connected to an end portion of spine 120. Bracket 170, which transversely outwardly extends from spine 120, defines a plurality of slots 180 therein capable of releasably engaging respective ones of a plurality of connectors 190 associated with device 10. Each connector 190, which may be threaded, is sized to receive the previously mentioned threaded nut 160 on an end portion thereof, when connector 190 has threads. In this case, threaded connector 190 is affixed to device 10 as threaded nut 160 threadably engages threaded connector 190. In this manner, spine 120 (and thus frame 110) is releasably connected to and supported by device 10, as described in more detail hereinbelow. Bracket 170 may be formed separately from spine 120 and integrally connected thereto by means of the previously mentioned bolt member 150 being threadably engaged by nut 160. Alternatively, bracket 170 may be integrally connected to spine 120 by being stamped from a single piece of material to avoid use of nuts and bolts. On the other hand, bracket 170 may be formed separately from spine 120 and integrally connected thereto by means of welding.

Referring to FIGS. 1, 2, 3, 4, 4A, 5, 6 and 7, first embodiment adjustable accessory 10 comprises a bendable or flexible strap 200 engageable with spine 120 (and thus engageable with frame 110). Strap 200 is sized to at least partially encircle container 40 for releasably connecting container 40 to spine 120 (and thus for releasably connecting container 40 to frame 110). Strap 200 may be formed from any suitable bendable or flexible material, such as leather, fabric, thin plastic strip or thin metal. Strap 200 has an aperture 210 alignable with a predetermined one of fasteners 140 for receiving the predetermined one of fasteners 140 therethrough as the predetermined one of fasteners 140 is received through a respective one of holes 130. In this manner, strap 200 may be adjustably selectively located along spine 120 at any one of holes 130. In addition, strap 200 may include a buckle arrangement 240 associated with strap 200. Thus, buckle arrangement 240, which is adjustable, tightens strap 200 about container 40 in order that container 40 is adjustably affixed to frame 110. Buckle arrangement 240 allows adjustable accessory 10 to accommodate various diameters of container 40. However, buckle arrangement 240 need not be present. Alternatively, strap 200 may be a "VELCRO" (registered trademark of the Velcro company) hook-and-loop material for securing strap 200 to frame 110. Use of a "VELCRO" material provides a quick-attach and quick-release capability for strap 200, so that container 40 may be quickly attached to and quickly released from frame 110. Thus, use of a "VELCRO" material avoids use of buckle arrangement 240. Hence, strap 200 intimately adjustably encircles or surrounds container 40 as strap 200 is affixed at a predetermined position on spine 120 for adjustably securing container 40 to frame 110. It may be appreciated from the teachings herein that strap 200 defines an adjustment mechanism coupled to frame 110. In addition, it may be appreciated from the teachings herein that strap 200 (i.e., the adjustment mechanism) is sized to adjustably surround various diameters of container 40, which is to be carried by frame 110. It may be further appreciated from the teachings herein that the adjustment mechanism adjustably locates container 40 on frame 110.

Figure 8:
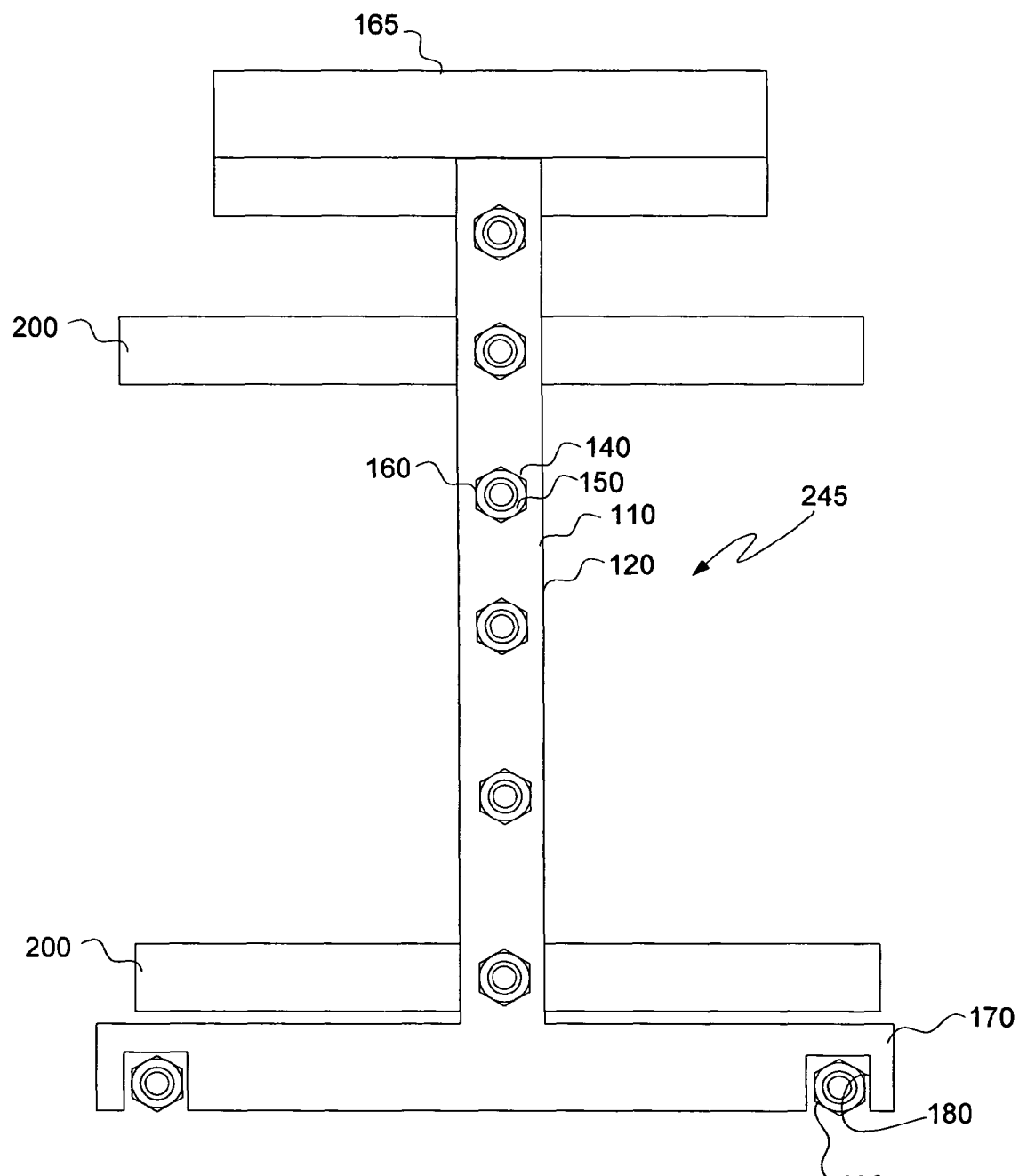
FIG. 8 is a front view in elevation of a second embodiment adjustable accessory.
Figure 9:
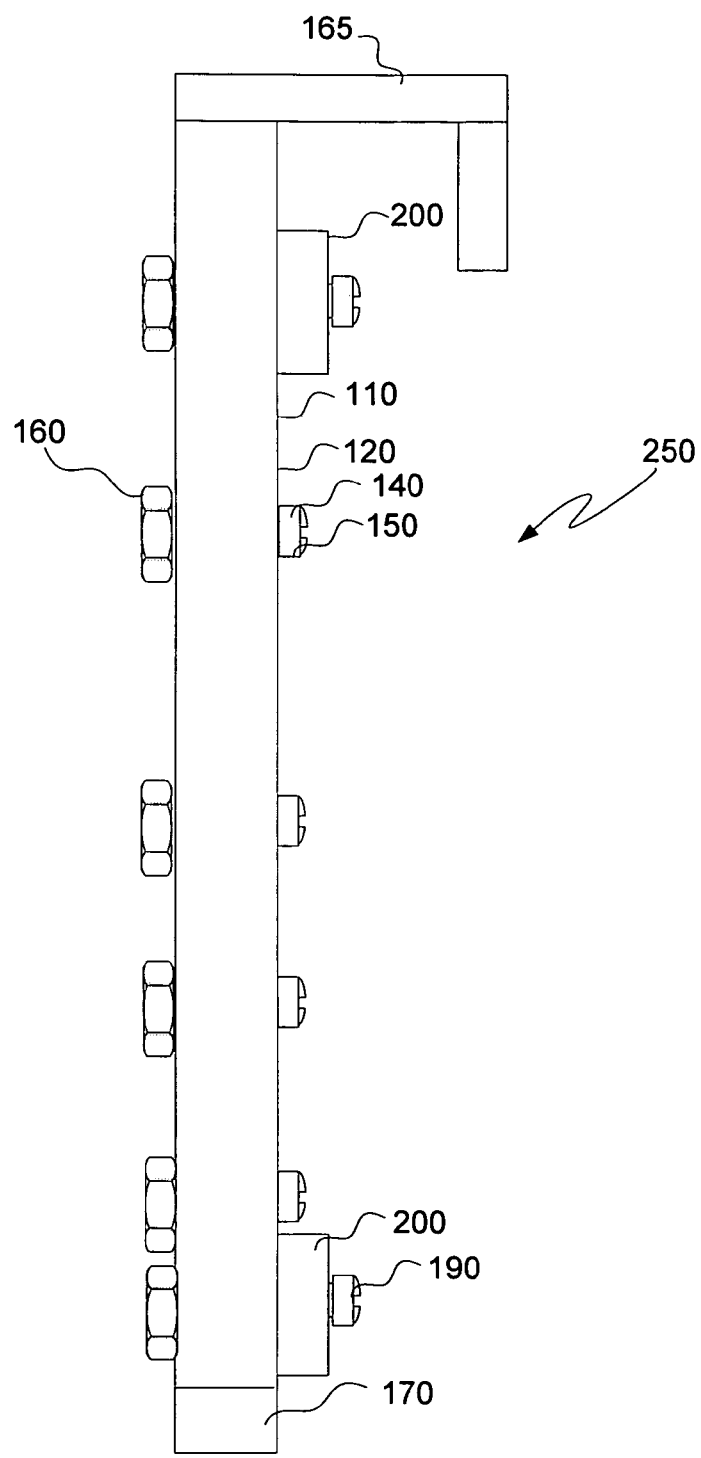
FIG. 9 is a side view in elevation of the second embodiment adjustable accessory.

Referring to FIGS. 8 and 9, there is shown a second embodiment adjustable accessory, generally referred to as 245. Second embodiment adjustable accessory 245 is substantially similar to first embodiment adjustable 10, except that bracket 170 is formed from a single piece of material and thus does not require fasteners 140 for attachment to spine 120.

Figure 9A:
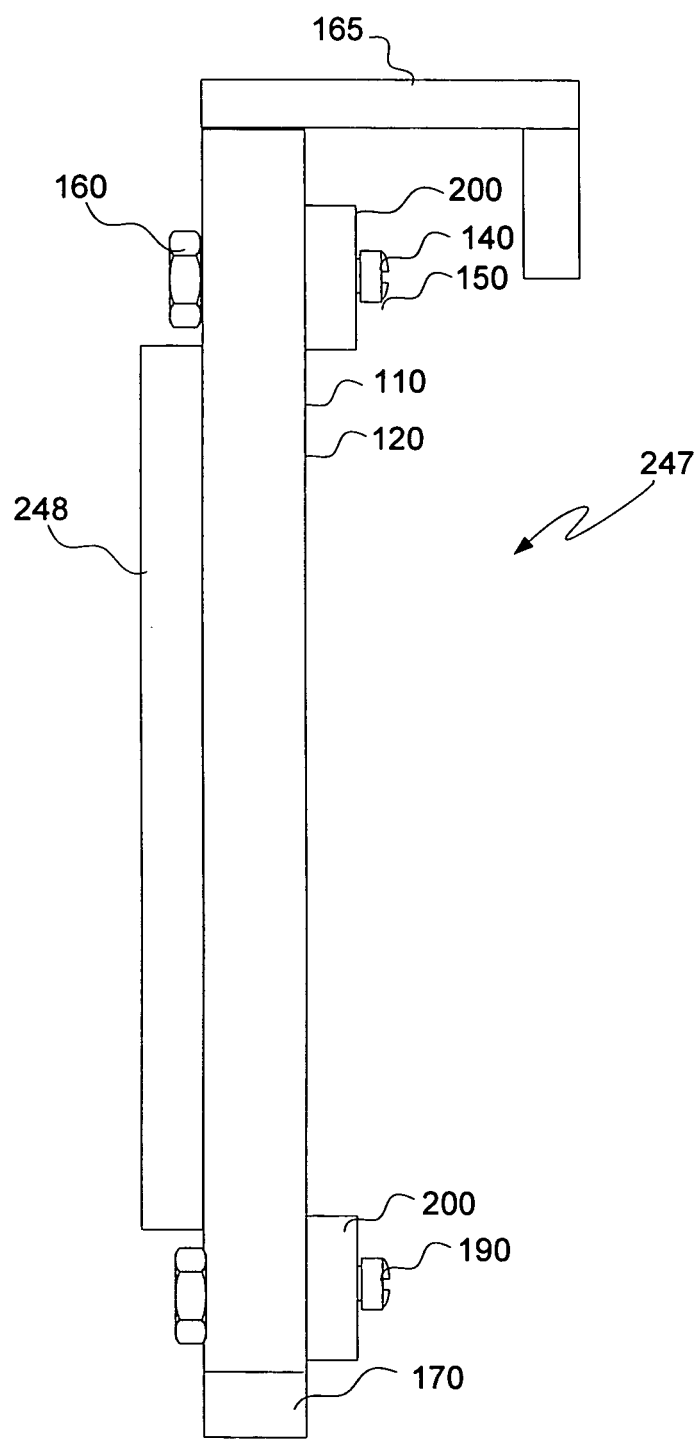
FIG. 9A is a side view in elevation of a third embodiment adjustable accessory.
Figure 9B:
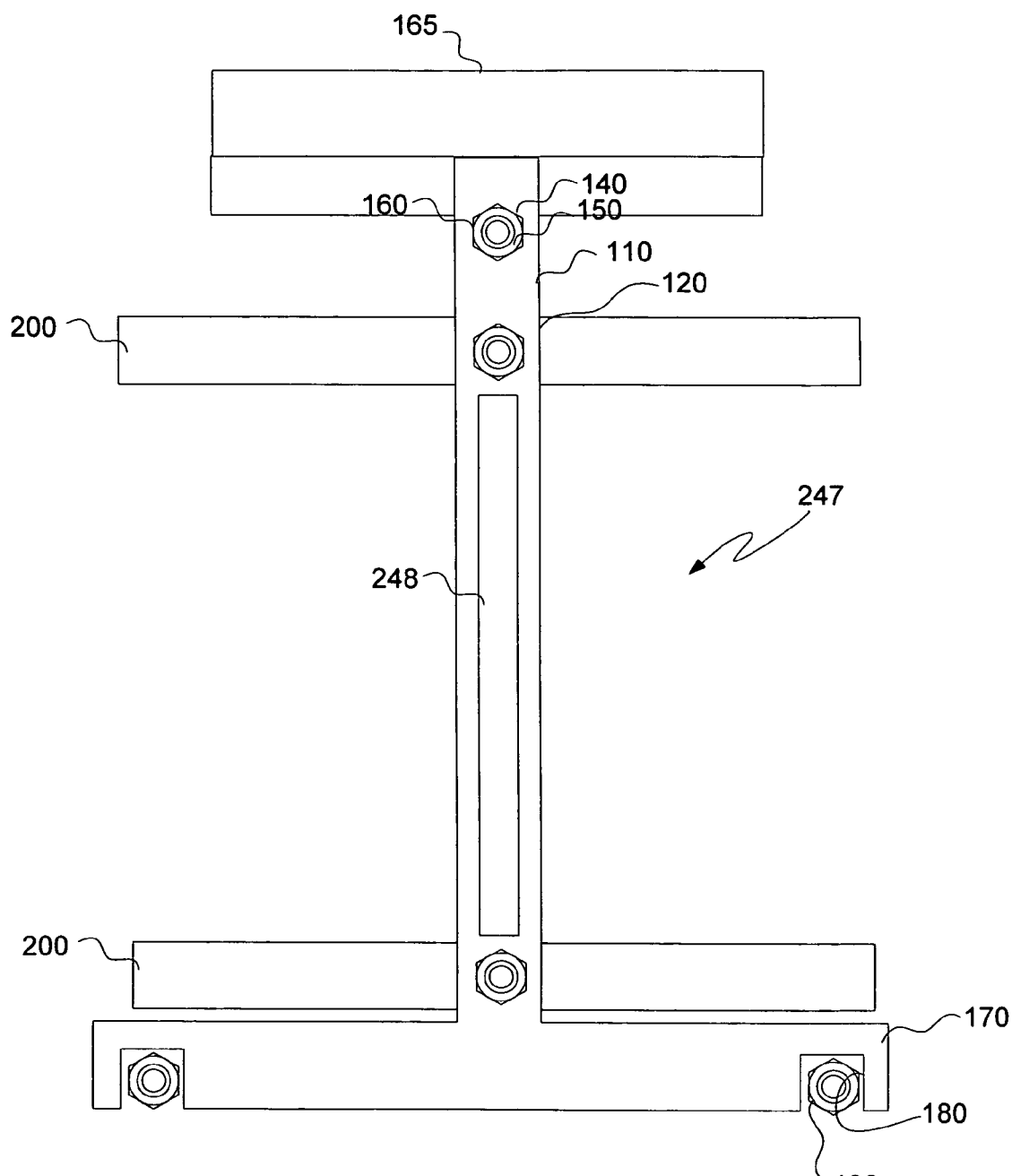
FIG. 9B is a front view in elevation of the third embodiment adjustable accessory.

Referring to FIGS. 9A and 9B, there is shown a third embodiment adjustable accessory, generally referred to as 247. Third embodiment adjustable accessory 247 is substantially similar to second embodiment adjustable 245, except that a vibration abatement member 248, such as a felt material, extends longitudinally along spine 120 to reduce vibration of container 40 against spine 120, as the mobile device moves.

Figure 10:
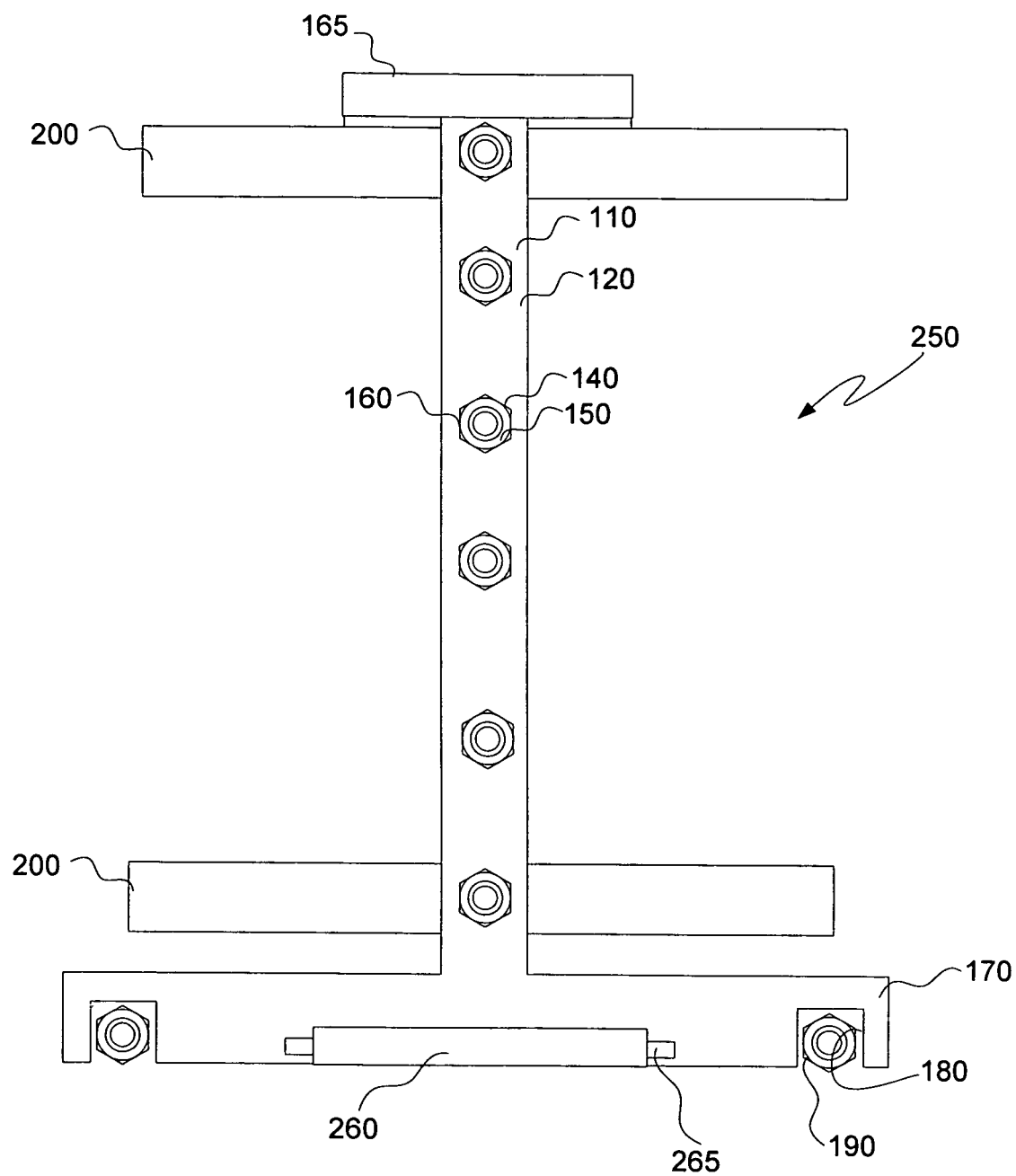
FIG. 10 is a front view in elevation of a fourth embodiment adjustable accessory.
Figure 11:
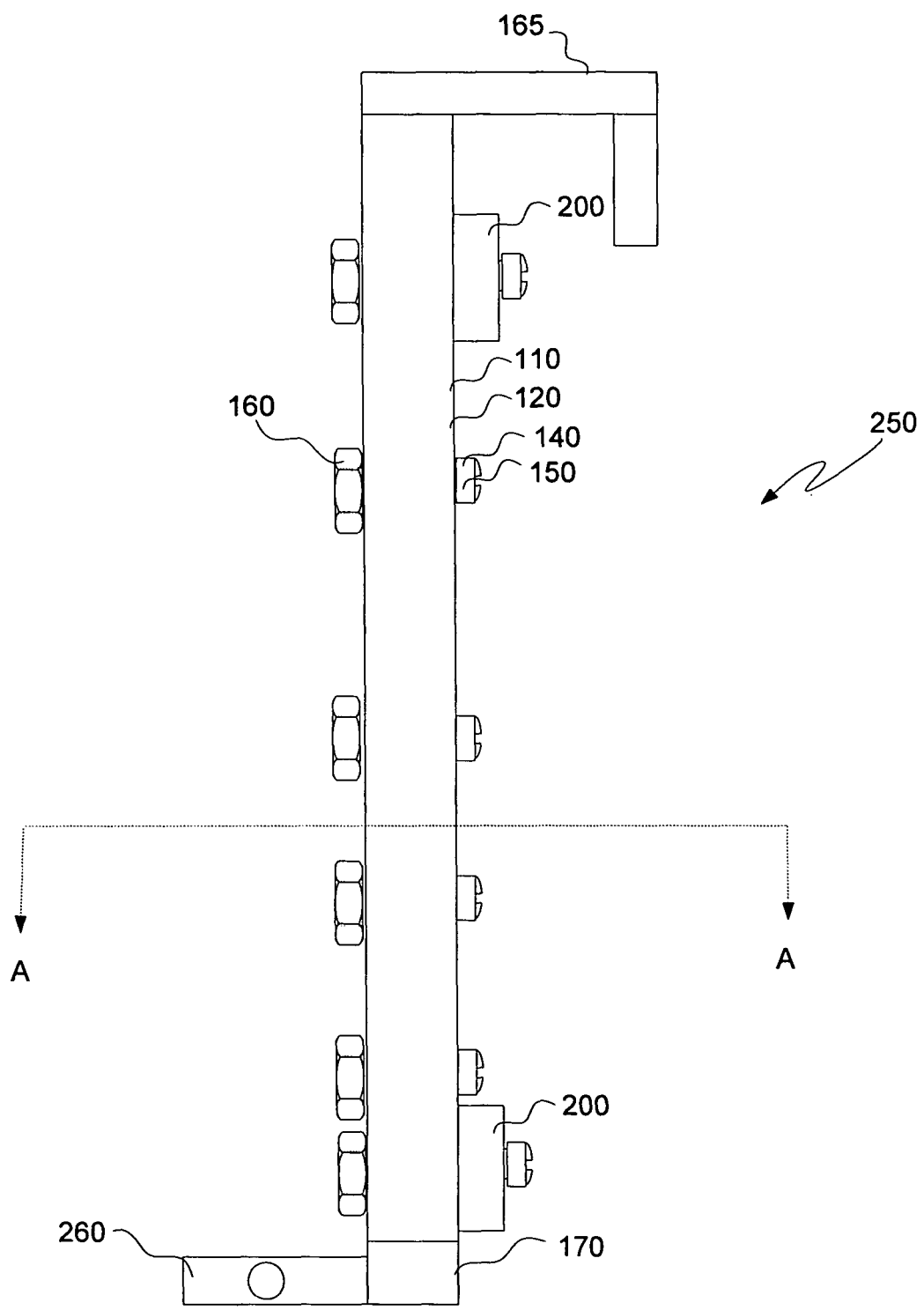
FIG. 11 is a side view in elevation of the fourth embodiment adjustable accessory.
Figure 11A:
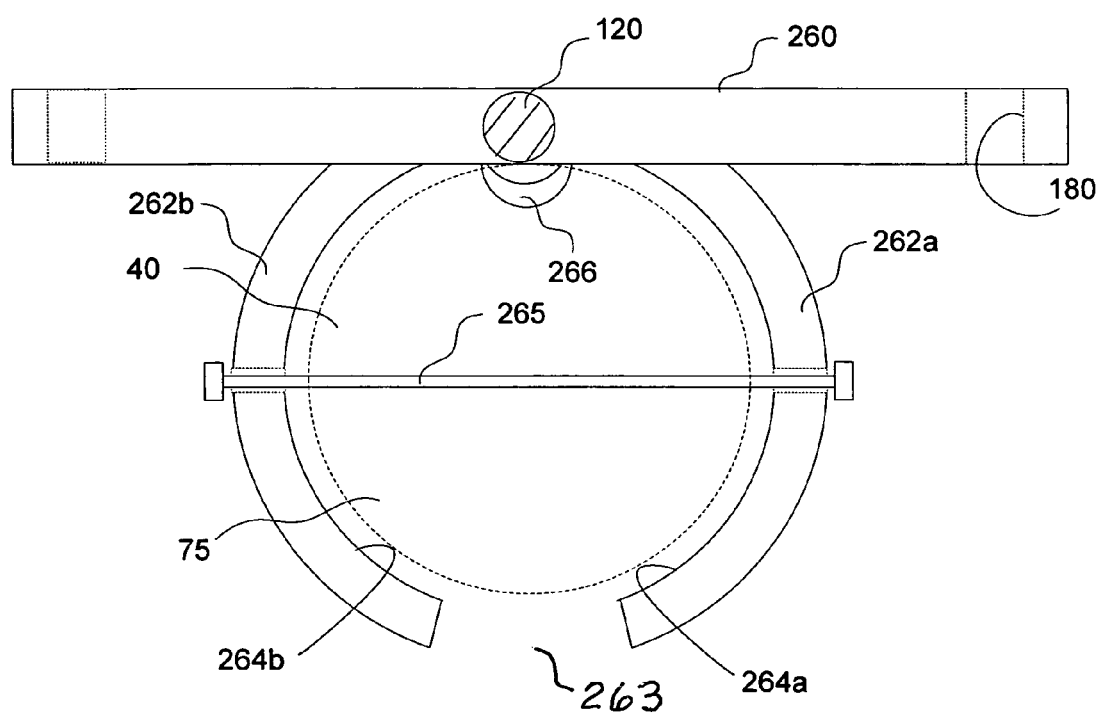
FIG. 11A is a view taken along section line A-A of FIG. 11.

Turning now to FIGS. 10, 11 and 11A, there is shown a fourth embodiment adjustable accessory, generally referred to as 250. Fourth embodiment adjustable accessory 250 is substantially similar to second embodiment adjustable accessory 245, except that fourth embodiment adjustable accessory 250 includes a fixed platform 260 integrally connected to spine 120. Fixed platform 260 is fixed in the sense that fixed platform 260 is immovable with respect to spine 120. The purpose of fixed platform 260 is to support the base portion 75 of container 40 thereon.

As best seen in FIG. 11A, fixed platform 260 comprises a pair of oppositely disposed arcuate members 262a and 262b defining a gap 263 between end portions thereof, as shown. Each arcuate member 262a and 262b defines an inner surface 264a and 264b thereon, respectively. Interconnecting arcuate members 262a and 262b is an elongate first support member 265, which may be a cable. Integrally connected to bracket 260 or to spine 120 is a second support member 266, which may be an inwardly projecting tab, as shown. First support member 265 and second support member 266 cooperate to support bottom portion 75 of container 40 when bottom portion of container 75 rests thereon. It may be understood that length of elongate first support member 265 may be selected or adjusted so as to bias arcuate members 262a and 262b toward each other so that inner surfaces 264a and 264b snugly embraces bottom portion 75 of container 40 in order to provide further support to bottom portion 75 of container 40.

Figure 12:
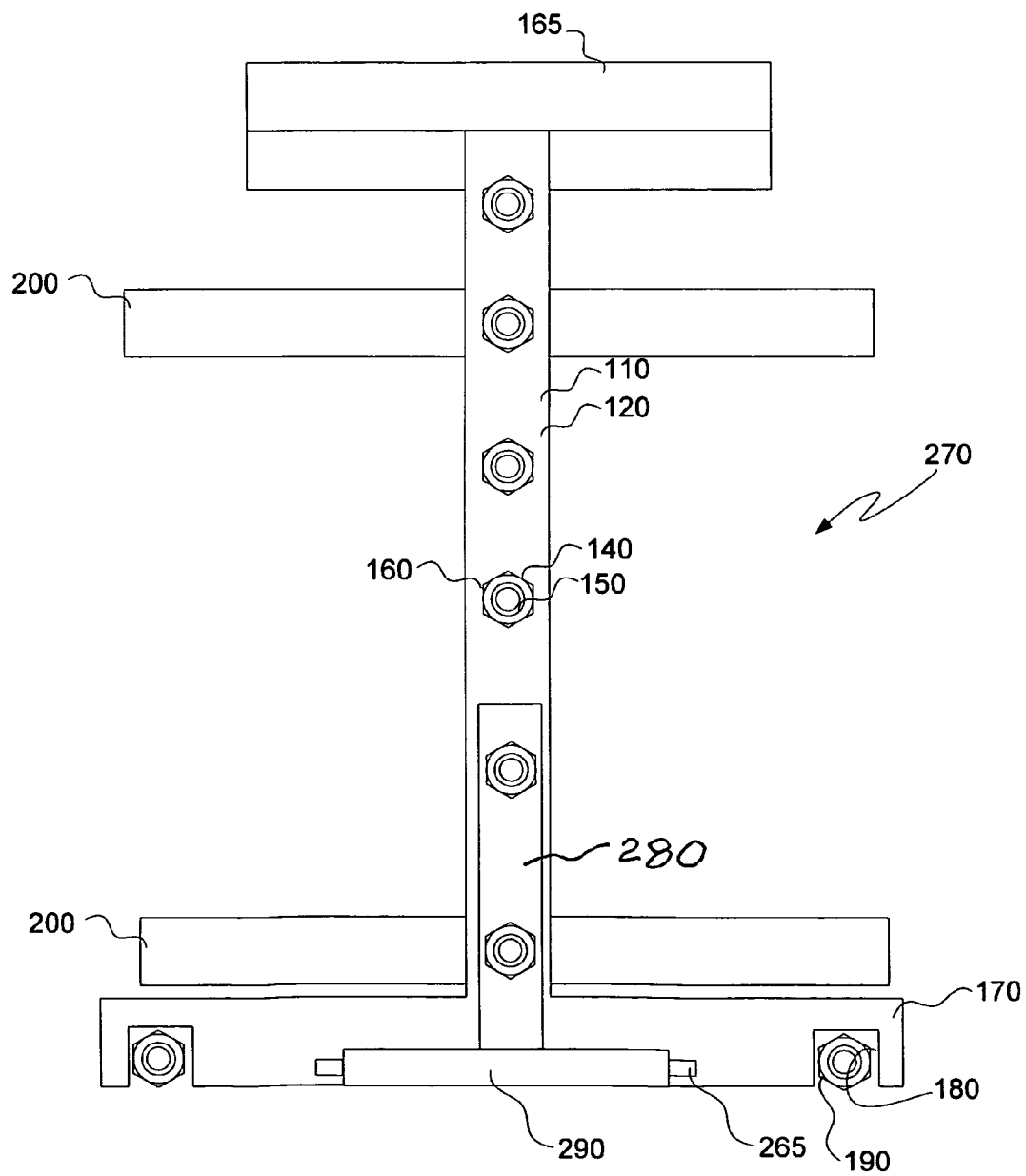
FIG. 12 is a front view in elevation of a fifth embodiment adjustable accessory.
Figure 13:
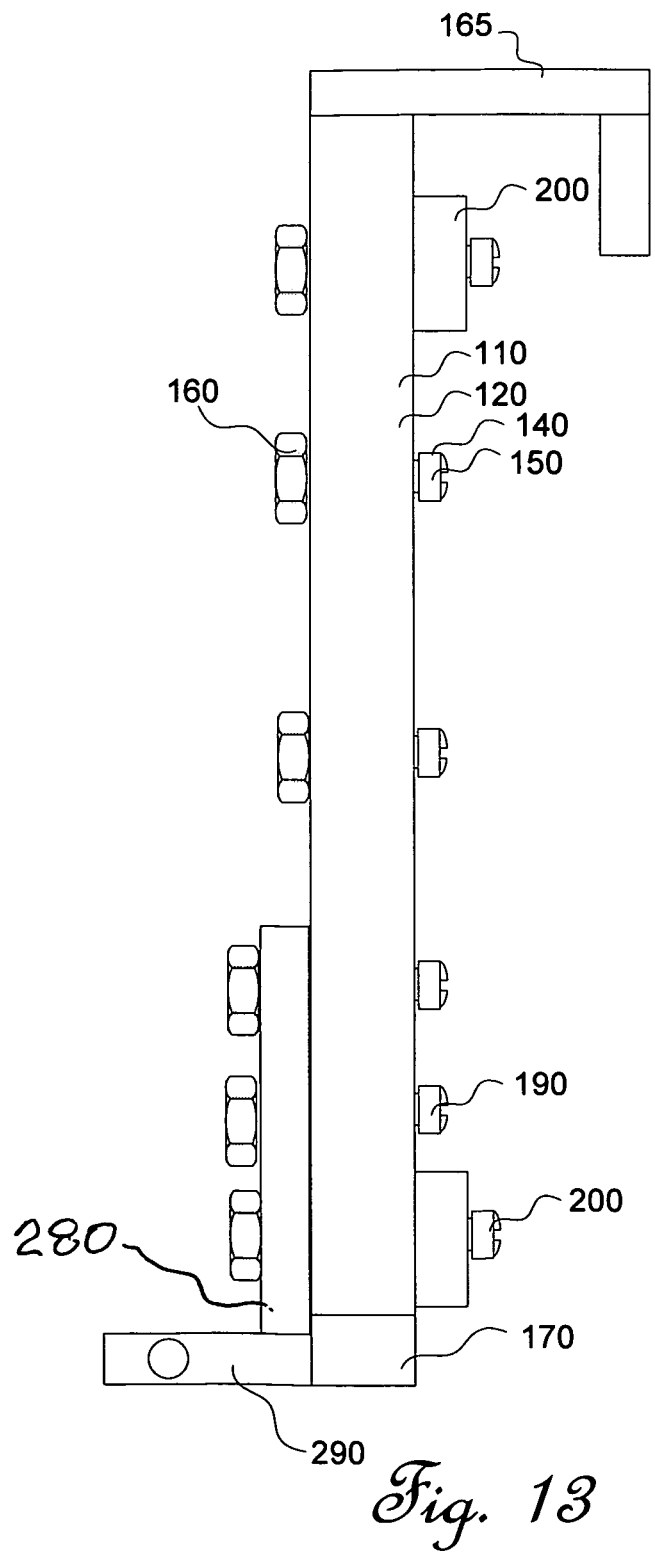
FIG. 13 is a side view in elevation of the fifth embodiment adjustable accessory.

Referring to FIGS. 12 and 13, there is shown a fifth embodiment adjustable accessory, generally referred to as 270. Fifth embodiment adjustable accessory 270 is substantially similar to third embodiment adjustable accessory 250, except that fifth embodiment adjustable accessory 270 includes a movable platform 280 connected to spine 120. Movable platform 280 is movable in the sense that movable platform 280 is movable with respect to spine 120. The purpose of movable platform 280 is to support the base portion 75 of container 40 thereon while allowing container 40 to be movable (i.e., repositioned) along spine 120. In this regard, movable platform 280 includes a support base 290 comprising the previously mentioned arcuate members 262a/262b and support members 265/266 for supporting base portion 75 of container 40 thereon. Support base 290 of movable platform 280 is integrally connected to a truss member 300 that is movably connected to spine 120 by means of any of fasteners 140. In this manner, movable platform 280 can be located at any one of holes 130 for adjustably locating container 40 along spine 120.

Thus, it may be appreciated from the teachings herein that first embodiment adjustable accessory 10, second embodiment adjustable accessory 245, third embodiment adjustable accessory 247, fourth embodiment adjustable accessory 250 and fifth embodiment adjustable accessory 270 accommodate containers of various diameters and lengths.

Returning to FIGS. 1 and 2, a first embodiment mobile device is there shown, generally referred to as 310, which is illustrated as a wheelchair to be operated by individual 30. First embodiment mobile device 310 includes any one of the previously mentioned embodiments of adjustable accessory 10/245/247/250/270. First embodiment mobile device 310 comprises a pair of transversely spaced-apart arm members 320a and 320b, which may have a pair of cushions 330a and 330b attached to respective ones of arm members 320a and 320b for resting the arms of individual 30 thereon as individual 30 occupies mobile device 310. Integrally connected to respective ones of arm members 320a and 320b are a pair of transversely spaced-apart, longitudinally extending leg members 340a and 340b. Each leg member 340a/340b engages a wheel assembly 350 (only one of which is shown). Wheel assemblies 350 are capable of pivoting about a longitudinal axis defined by each leg member 340a and 340b for allowing individual 30 to change direction of mobile device 310 as individual 30 operates mobile device 310 on a surface 355. Mobile device 310 may further comprise a pair of handholds 360a and 360b integrally connected to respective ones of a pair of transversely spaced-apart, longitudinally extending rails 370a and 370b. Integrally interconnecting respective ones of rails 370a and 370b and leg members 340a and 340b is a pair of struts 380a and 380b. In this manner, arm members 320a/b, leg members 340a/b, rails 370a/b, and struts 380a/380b are interconnected to provide structural integrity to first embodiment mobile device 310. A brace 390 interconnecting struts 380a/b may also be provided to enhance the structural integrity of mobile device 310, if desired. In addition, a pair of wheels 400a and 400b are rotatably connected to respective ones of rails 370a/b in any suitable manner to allow mobile device to be movable on surface 355. Moreover, mobile device 310 suitably includes a back panel 402, a pair of side panels 404 (only one of which is shown) and a seat cushion 406 for comfortably accommodating individual 30 when seated in mobile device 310.

Figure 3:
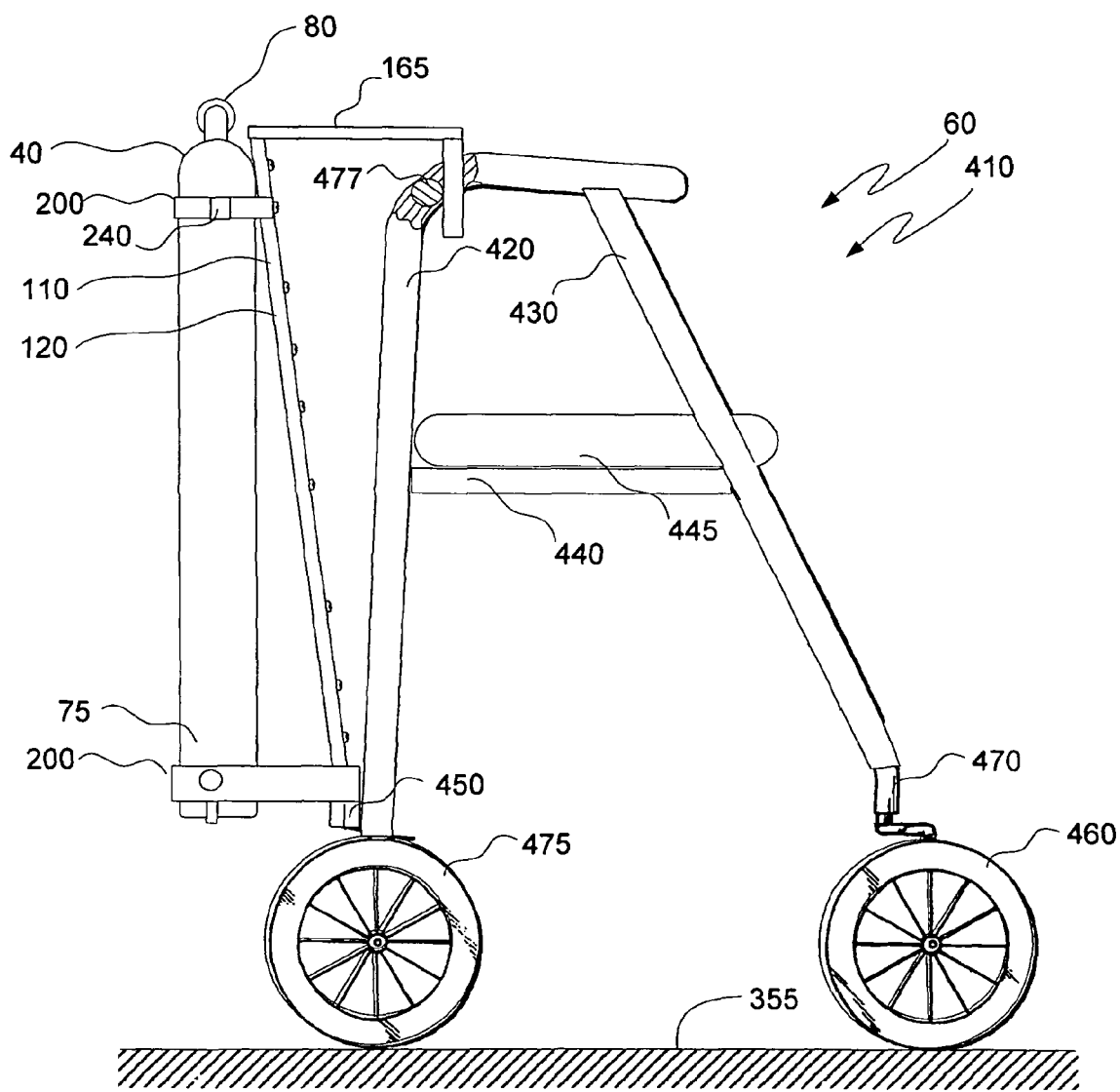
FIG. 3 is a view in elevation of the first embodiment adjustable accessory connected to a second embodiment mobile device.

As best seen in FIG. 3, a second embodiment mobile device is there shown, generally referred to as 410, which is illustrated as a walker to be operated by individual 30. Second embodiment mobile device 410 includes any one of the previously mentioned embodiments of adjustable accessory 10/245/247/250/270. Second embodiment mobile device 410 comprises a pair of transversely spaced-apart, substantially longitudinally extending first bars 420 (only one of which is shown) that are integrally connected to a pair of transversely spaced-apart, substantially longitudinally extending second bars 430 (only one of which is shown). Interconnecting respective ones of first bars 420 and second bars 430 is a planer member 440 upon which a seat cushion 445 may be placed. It may be appreciated by a person of ordinary skill in the art, that, based on the teachings herein, any one of the previously mentioned embodiments of adjustable accessory 10/245/247/250/270 may be attached to first bars 420 by fasteners 140, such as at location 450. In addition, second embodiment mobile device 410 comprises a first pair of wheels 460 (only one of which is shown) pivotally connected to respective ones of second bars 30, such as by a respective pair of pivot mechanisms 470 (only one of which is shown) for changing direction of mobile device 410 as mobile device 410 rolls on surface 355. Second embodiment mobile device 410 further comprises a second pair of wheels 475 for rolling mobile device 410 on surface 355. In addition, previously mentioned J-shaped or L-shaped hook member 165 engages a cross-member 477 that interconnects-first bars 420 for further securing frame 10 to second embodiment mobile device 410.

Figure 4:
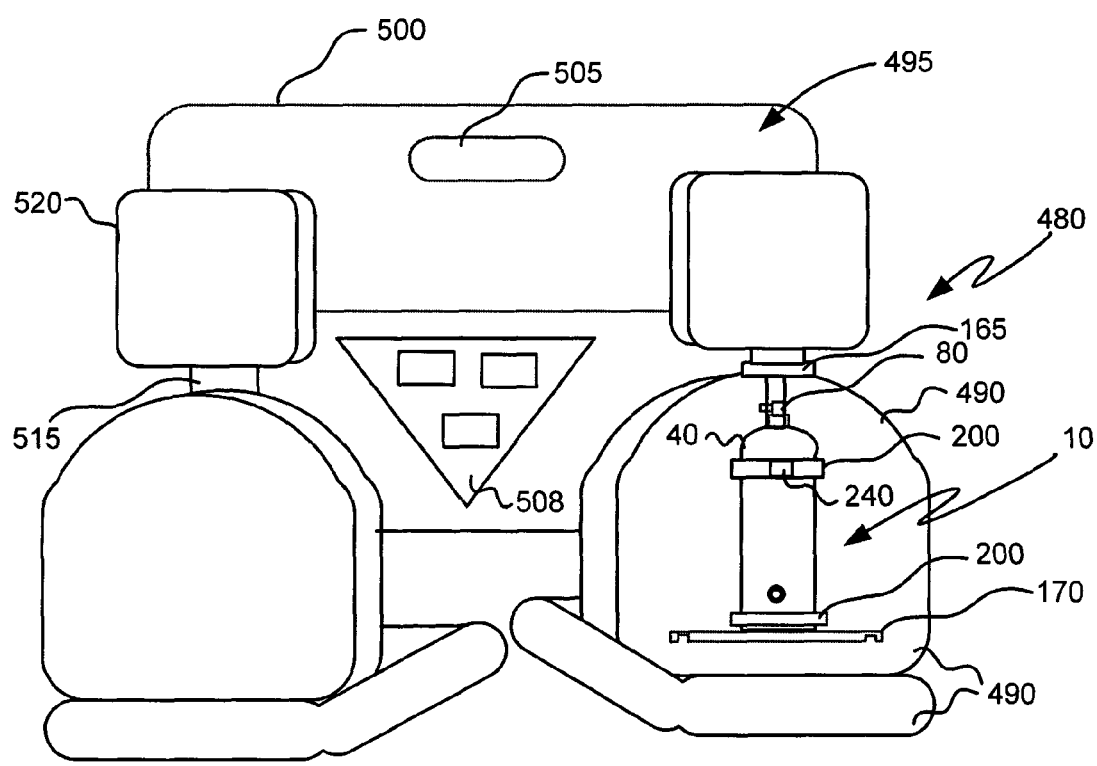
FIG. 4 is a view in perspective of the first embodiment adjustable accessory connected to a third embodiment mobile device.
Figure 4A:
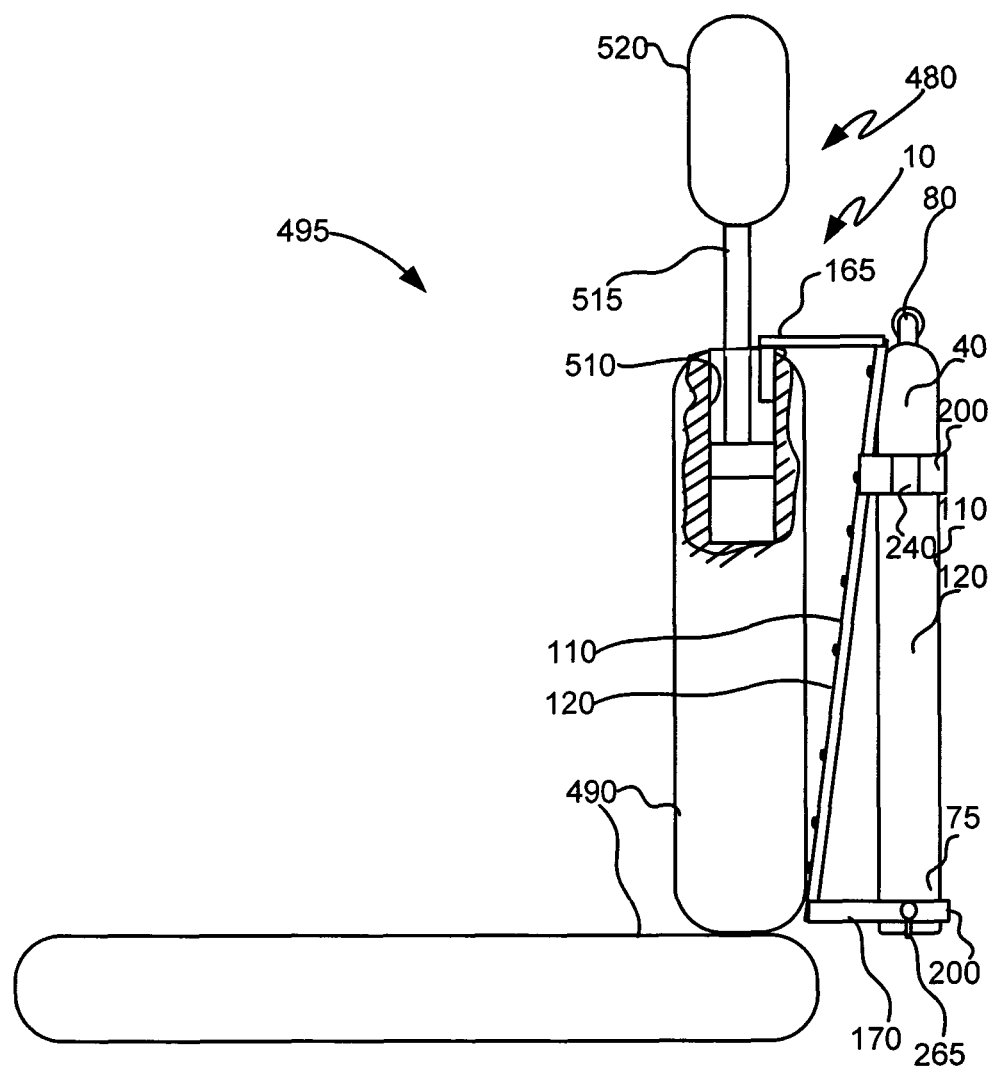
FIG. 4A is a side view in elevation of the first adjustable accessory connected to the third embodiment mobile device.
Figure 5:
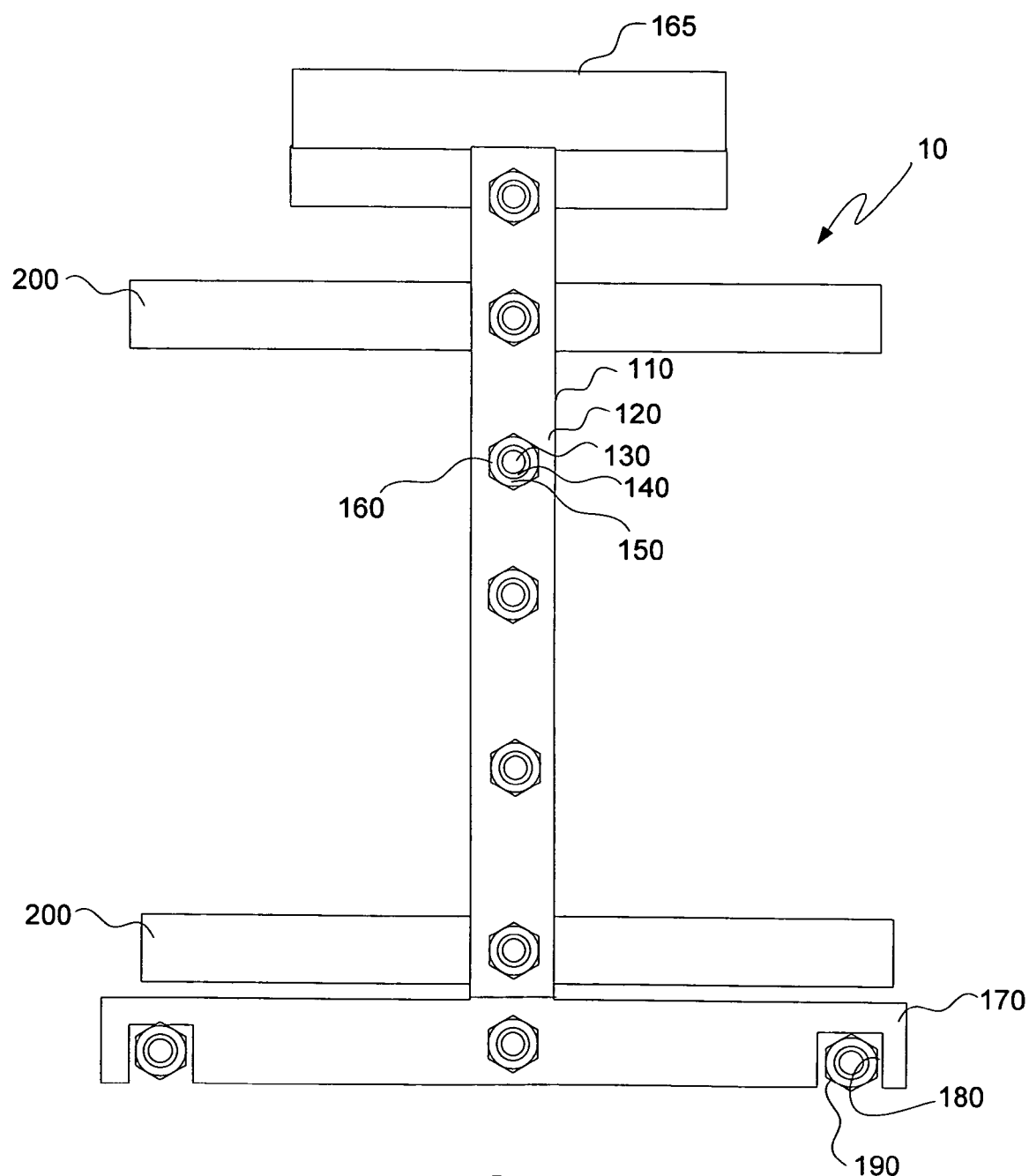
FIG. 5 is a front view in elevation of the first embodiment adjustable accessory.
Figure 6:
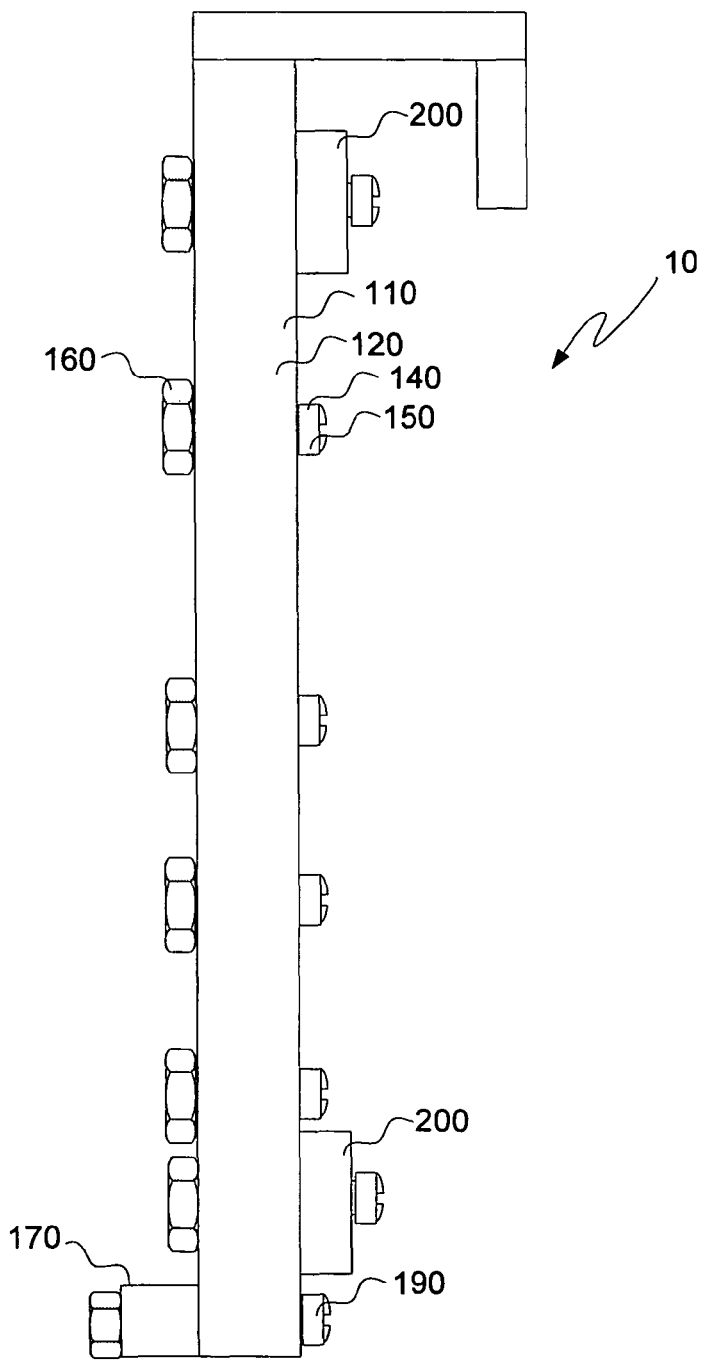
FIG. 6 is a side view in elevation of the first embodiment adjustable accessory.
Figure 7:
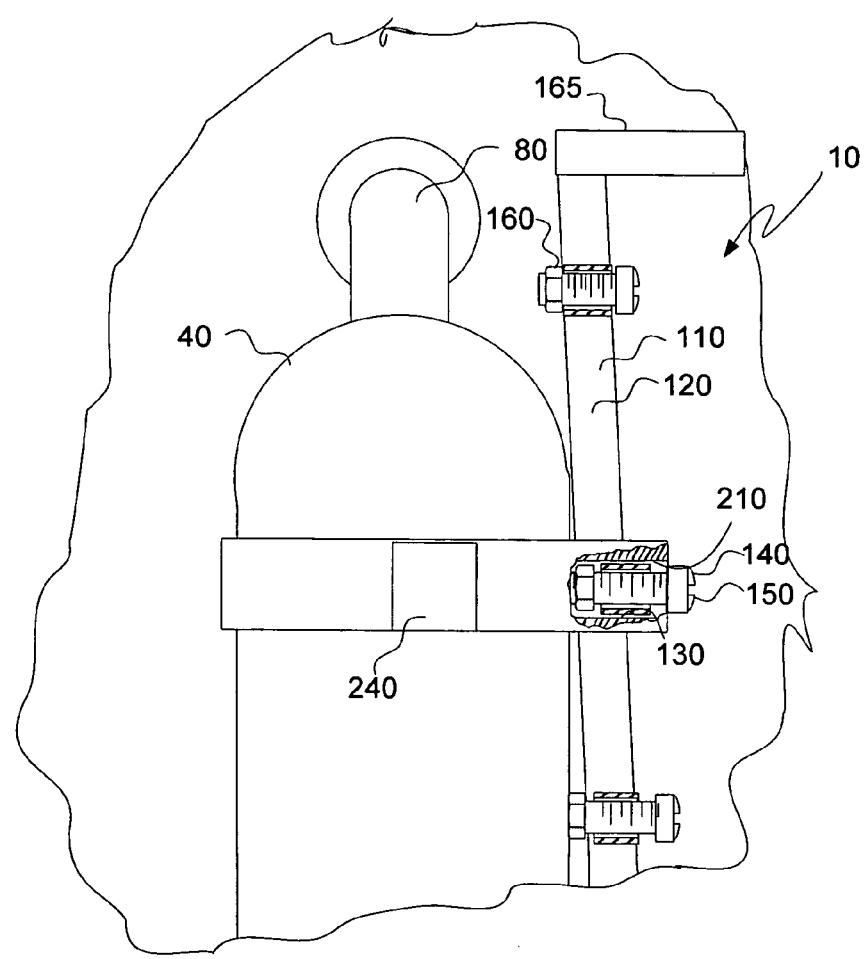
FIG. 7 is a fragmentation view in elevation of an adjustable strap releaseably connected to an elongate spine belonging to the first embodiment adjustable accessory, the strap at least partially encircling a container.

As illustrated in FIGS. 4 and 4A, a third embodiment mobile device is there shown, generally referred to as 480, which is illustrated as a vehicle seat 490 to be occupied by individual 30. It is understood that vehicle seat 490 is disposed in vehicular space 495 opposite a windshield 500, a rear view mirror 505 and an instrument panel or a dashboard 508, as illustrated. Third embodiment mobile device 480 includes any one of the previously mentioned embodiments of adjustable accessory 10/245/247/250/270. In this regard, vehicle seat 490 defines a seat cavity 510 that slidably receives a headrest extension 515 that is connected to a headrest 520. Previously mentioned J-shaped or L-shaped hook member 165 is received in seat cavity 510 for securely connecting any of the embodiments of adjustable accessory 10/245/247/250/270 to vehicle seat 490.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken as limiting. For example, any one of adjustable accessories 10/245/247/250/270 is shown adjustably connected to any one of mobile devices 310/410/480. However, it should be understood that any one of adjustable accessories 10/245/247/250/270 may be suitably connected to the back of emergency personnel, such as a fireman, for providing a supply of oxygen to be used while attending to an emergency in an oxygen deficient environment.

Moreover, those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated or claimed, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Therefore, what is provided is an adjustable accessory for attachment to a device that enhances mobility of an individual and method of assembling same.

Moreover, the various aspects and embodiments disclosed herein are for purposes of illustration and are not intended to be limiting, with the true scope and spirit being indicated by the following claims.

What is claimed is:

1. An adjustable accessory for attachment to a device that enhances mobility of an individual, comprising:
   (a) a frame capable of being coupled to the device;
   (b) an adjustment mechanism coupled to said frame, said adjustment mechanism capable of being sized to adjustably surround a container to be carried by said frame and capable of adjustably locating the container on said frame; and
   (c) a platform coupled to said frame for adjustably supporting the container, said platform including a cable adapted to support the container while the container rests thereon.

2. An adjustable accessory for attachment to a device that enhances mobility of an individual, comprising:
   (a) a frame having a plurality of holes for receiving respective ones of a plurality of fasteners;
   (b) a strap engageable with said frame and a container for coupling the container to said frame, said strap having an aperture for receiving a predetermined one of the fasteners as the predetermined one of the fasteners is received in a respective one of the holes, whereby said strap is adjustably affixed to said frame as the predetermined one of the fasteners is received by the aperture; and
   (c) an adjustable platform coupled to said frame for adjustably supporting the container, said platform including a cable adapted to support the container while the container rests thereon.

3. The adjustable accessory of claim 2, wherein said strap is adjustable.

4. An adjustable accessory for attachment to a device that enhances mobility of an individual while the adjustable accessory securely carries a container, comprising:
(a) a frame having a plurality of holes for receiving respective ones of a plurality of fasteners therethrough;
(b) a strap engageable with said frame and capable of at least partially encircling the container for coupling the container to said frame, said strap having an aperture for receiving a predetermined one of the fasteners therethrough as the predetermined one of the fasteners is received through a respective one of the holes, whereby said strap is adjustably affixed to said frame as the predetermined one of the fasteners is received through the aperture; and
(c) an adjustable platform adjustably coupled to said frame for adjustably supporting the container on said frame, said platform including a cable adapted to support the container while the container rests thereon.

5. The adjustable accessory of claim 4, wherein said strap is adjustable for adjustably affixing said strap to said frame.

6. The adjustable accessory of claim 4, wherein said frame comprises:
(a) an elongate spine having an end portion; and
(b) a bracket integrally connected to the end portion of said spine and outwardly extending therefrom, said bracket defining a slot therein capable of releasably engaging a connector associated with the device for connecting said spine to the device.

7. A device that enhances mobility of an individual, comprising an adjustable accessory, including:
(a) a frame capable of being coupled to the device;
(b) an adjustment mechanism coupled to said frame, said adjustment mechanism capable of being sized to adjustably surround a container to be carried by said frame and capable of adjustably locating the container on said frame; and
(c) a platform coupled to said frame for adjustably supporting the container, said platform including a cable adapted to support the container while the container rests thereon.

8. A device that enhances mobility of an individual, comprising an adjustable accessory, including:
(a) a frame having a plurality of holes for receiving respective ones of a plurality of fasteners;
(b) a strap engageable with said frame and the container for coupling the container to said frame, said strap having an aperture for receiving a predetermined one of the fasteners as the predetermined one of the fasteners is received in a respective one of the holes, whereby said strap is adjustably affixed to said frame as the predetermined one of the fasteners is received by the aperture; and
(c) an adjustable platform coupled to said frame for supporting the container, said platform including a cable adapted to support the container while the container rests thereon.

9. The device of claim 8, wherein said strap is adjustable.

10. A device that enhances mobility of an individual, comprising an adjustable accessory capable of securely carrying a container, including:
(a) a frame having a plurality of holes for receiving respective ones of a plurality of fasteners therethrough;
(b) a strap engageable with said frame and capable of at least partially encircling the container for coupling the container to said frame, said strap having an aperture for receiving a predetermined one of the fasteners therethrough as the predetermined one of the fasteners is received through a respective one of the holes, whereby said strap is adjustably affixed to said frame as the predetermined one of the fasteners is received through the aperture; and
(c) an adjustable platform coupled to said frame for adjustably supporting the container on said frame, said platform including a cable adapted to support the container while the container rests thereon.

11. The device of claim 10, wherein said strap is adjustable for adjustably affixing said strap to said frame.

12. The device of claim 10, wherein said frame includes:
(a) an elongate spine having an end portion; and
(b) a bracket integrally connected to the end portion of said spine and outwardly extending therefrom, said bracket defining a slot therein capable of releasably engaging a connector associated with the device for connecting said spine to the device.

13. A method of assembling an adjustable accessory for attachment to a device that enhances mobility of an individual, comprising:
(a) providing a frame capable of being coupled to the device;
(b) coupling an adjustment mechanism to the frame, the adjustment mechanism capable of being sized to adjustably surround a container to be carried by the frame and capable of adjustably locating the container on the frame; and
(c) coupling a platform to the frame for adjustably supporting the container, the platform including a cable adapted to support the container while the container rests thereon.

14. A method of assembling an adjustable accessory for attachment to a device that enhances mobility of an individual, comprising:
(a) providing a frame having a plurality of holes for receiving respective ones of a plurality of fasteners;
(b) engaging a strap with the frame and the container for coupling the container to the frame, the strap having an aperture for receiving a predetermined one of the fasteners as the predetermined one of the fasteners is received in a respective one of the holes, whereby the strap is adjustably affixed to the frame as the predetermined one of the fasteners is received by the aperture; and
(c) coupling an adjustable platform to the frame for adjustably supporting the container, the platform including a cable adapted to support the container while the container rests thereon.

15. The method of claim 14, wherein engaging the strap with the frame and the container comprises engaging an adjustable strap with the frame and the container.

16. A method of assembling an adjustable accessory for attachment to a device that enhances mobility of an individual while the adjustable accessory securely carries a container, comprising:
(a) providing a frame having a plurality of holes for receiving respective ones of a plurality of fasteners therethrough;
(b) engaging a strap with the frame, the strap capable of at least partially encircling the container for coupling the container to the frame, the strap having an aperture for receiving a predetermined one of the fasteners therethrough as the predetermined one of the fasteners is received through a respective one of the holes, whereby the strap is adjustably affixed to the frame as the predetermined one of the fasteners is received through the aperture; and (c) connecting an adjustable platform to the frame for adjustably supporting the container on the frame, the platform including a cable adapted to support the container while the container rests thereon.

17. The method of claim 16, wherein engaging the strap with the frame comprises engaging an adjustable strap with the frame for adjustably engaging the strap with the frame.

18. The method of claim 16, wherein providing a frame comprises:
   (a) providing an elongate spine having an end portion; and
   (b) integrally connecting a bracket to the end portion of the spine, the bracket outwardly extending therefrom and defining a slot therein capable of releasably engaging a connector associated with the device for connecting the spine to the device.

19. An adjustable accessory for attachment to a device that enhances mobility of an individual while the adjustable accessory securely carries a container having a substance therein of medicinal benefit to the individual, comprising:
   (a) a frame having a plurality of holes for receiving respective ones of a plurality of fasteners;
   (b) a strap engageable with said frame and sized to at least partially encircle the container for connecting the container to said frame, said strap having an aperture therethrough alignable with a predetermined one of the fasteners for receiving the predetermined one of the fasteners therethrough as the predetermined one of the fasteners is received through a respective one of the holes, whereby said strap is adjustably affixed to said frame as the predetermined one of the fasteners is received through the aperture and whereby the container is adjustably securely carried by said frame as the predetermined one of the fasteners is received through the respective one of the holes and as said strap is adjustably affixed to said frame; and
   (c) an adjustable platform integrally connected to said frame for adjustably supporting the container on said platform, said platform including a cable adapted to support the container while the container rests thereon.

20. A device that enhances mobility of an individual, comprising an adjustable accessory capable of securely carrying a container having a substance therein of medicinal benefit to the individual, including:
   (a) a frame having a plurality of holes for receiving respective ones of a plurality of fasteners therethrough;
   (b) a strap engageable with said frame and sized to at least partially encircle the container for connecting the container to said frame, said strap having an aperture therethrough alignable with a predetermined one of the fasteners for receiving the predetermined one of the fasteners therethrough as the predetermined one of the fasteners is received through a respective one of the holes, whereby said strap is adjustably affixed to said frame as the predetermined one of the fasteners is received through the aperture and whereby the container is adjustably securely carried by said frame as the predetermined one of the fasteners is received through the respective one of the holes and as said strap is adjustably affixed to said frame; and
   (c) an adjustable platform integrally connected to said frame for adjustably supporting the container on said platform, said platform including a cable adapted to support the container while the container rests thereon.

21. A method of assembling an adjustable accessory for attachment to a device that enhances mobility of an individual while the accessory securely carries a container having a substance therein of medicinal benefit to the individual, comprising:
   (a) providing a frame having a plurality of holes for receiving respective ones of a plurality of fasteners therethrough;
   (b) engaging a strap with the frame, the strap sized to at least partially encircle the container for connecting the container to the frame, the strap having an aperture therethrough alignable with a predetermined one of the fasteners for receiving the predetermined one of the fasteners therethrough as the predetermined one of the fasteners is received through a respective one of the holes, whereby the strap is adjustably affixed to the frame as the predetermined one of the fasteners is received through the aperture and whereby the container is adjustably securely carried by the frame as the predetermined one of the fasteners is received through the respective one of the holes and as the strap is adjustably affixed to the frame; and
   (c) integrally connecting an adjustable platform to the frame for adjustably supporting the container on the platform, the platform including a cable adapted to support the container while the container rests thereon.

\* \* \* \* \*